US008687180B2

(12) United States Patent
Cohen

(10) Patent No.: US 8,687,180 B2
(45) Date of Patent: Apr. 1, 2014

(54) SYSTEM, METHOD, AND DEVICE FOR DETERMINING A FOCAL POSITION OF AN OBJECTIVE IN A MICROSCOPY IMAGING SYSTEM

(75) Inventor: Avrum I. Cohen, Downingtown, PA (US)

(73) Assignee: Molecular Devices, LLC, Sunnyvale, CA (US)

( * ) Notice: Subject to any disclaimer, the term of this patent is extended or adjusted under 35 U.S.C. 154(b) by 0 days.

(21) Appl. No.: 13/491,017

(22) Filed: Jun. 7, 2012

(65) Prior Publication Data

US 2013/0329233 A1    Dec. 12, 2013

(51) Int. Cl.
G01B 9/00 (2006.01)
G01M 11/02 (2006.01)

(52) U.S. Cl.
CPC .......... *G01M 11/0228* (2013.01); *G06F 7/706* (2013.01)
USPC .......................................... 356/125; 356/124

(58) Field of Classification Search
CPC .......................... G01M 11/0228; G03F 7/706
USPC .............................................................. 356/125
See application file for complete search history.

(56) References Cited

U.S. PATENT DOCUMENTS

| | | | |
|---|---|---|---|
| 6,956,695 B2 | 10/2005 | Tafas et al. | |
| 7,274,433 B2 * | 9/2007 | Harada | 355/30 |
| 7,345,814 B2 | 3/2008 | Yoneyama et al. | |
| 7,646,482 B2 * | 1/2010 | Jiang | 356/326 |
| 2003/0179387 A1 * | 9/2003 | Uno et al. | 356/624 |
| 2006/0022114 A1 * | 2/2006 | Kennedy et al. | 250/201.3 |
| 2008/0054156 A1 * | 3/2008 | Fomitchov | 250/201.3 |
| 2008/0099661 A1 * | 5/2008 | Virag et al. | 250/201.3 |
| 2010/0060883 A1 * | 3/2010 | Heiden | 356/126 |

FOREIGN PATENT DOCUMENTS

WO    WO2012/025220    3/2012

OTHER PUBLICATIONS

International Search Report from the International Patent Application No. PCT/US2013/044334, dated Sep. 2, 2013.
WIPO Patentscope snapshot translation of European Patent No. 2011004227.

* cited by examiner

*Primary Examiner* — Michael P Stafira
(74) *Attorney, Agent, or Firm* — Bella Fishman

(57) ABSTRACT

A system and method of determining a focal position for an objective positioned at a measurement location of a sample holder in a microscopy imaging system are provided. The objective is moved to a position relative to the sample holder that corresponds to a distance between the objective and the sample holder. The sample holder has a conditioned upper surface. A focusing light beam is projected onto the sample holder when the objective is located at the position, and the objective focuses the focusing light beam on the sample holder. A reflected light beam resulting from reflection of the focusing light beam off the conditioned upper surface is observed. The focal position for the objective is determined based on the reflected light beam such that the objective produces an in focus image of a microscopy sample when the objective is located at the focal position.

18 Claims, 9 Drawing Sheets

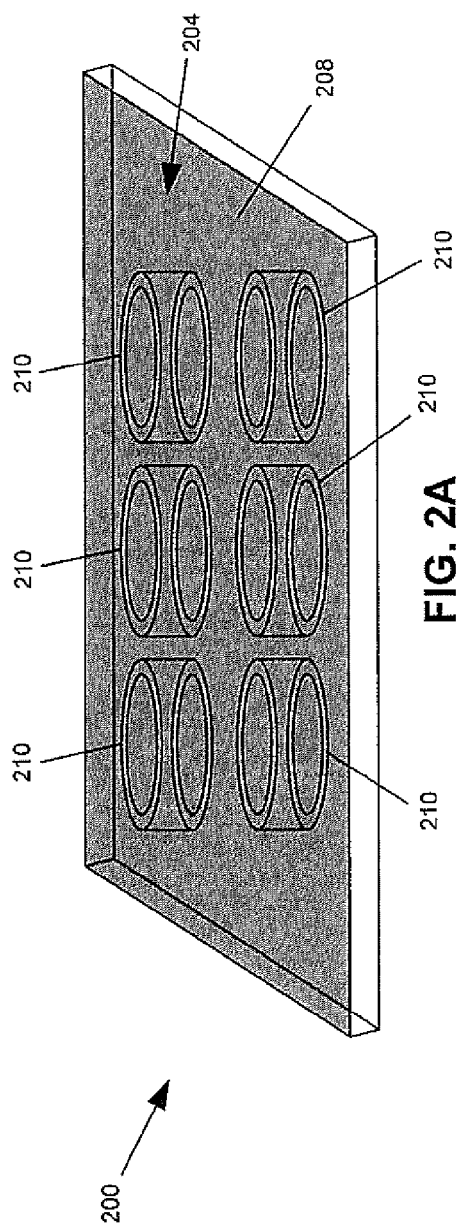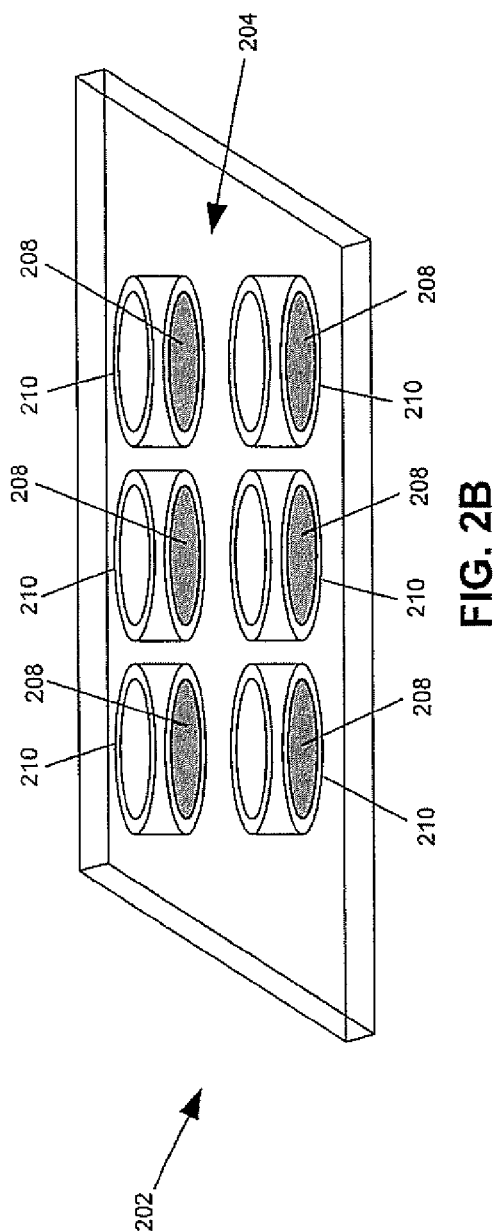
FIG. 2A
FIG. 2B

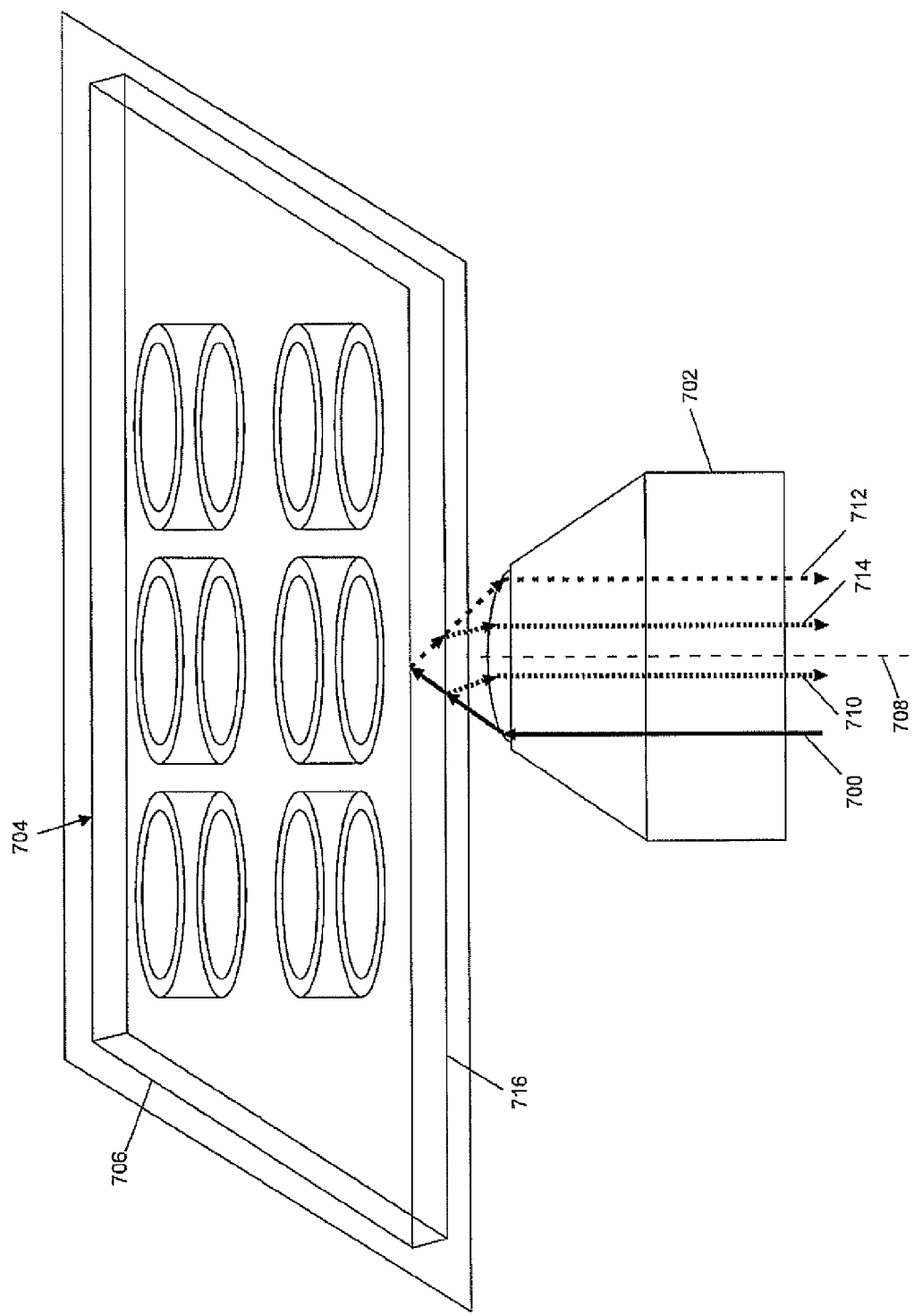

SYSTEM, METHOD, AND DEVICE FOR DETERMINING A FOCAL POSITION OF AN OBJECTIVE IN A MICROSCOPY IMAGING SYSTEM

FIELD OF THE INVENTION

This invention relates to automated and semi-automated microscopy for cell biology and other similar research and in particular relates to high content screening microscopy imaging systems.

BACKGROUND

Researchers may use microscopy imaging systems during high-content screenings (HCS) to obtain images of microscopy samples. A sample holder—e.g., a microtitre plate, slide, dish, etc.—may support the microscopy samples during the screening process. Microscopy imaging systems may include an adjustable objective to produce the images of the microscopy samples. The position of the objective relative to the sample holder may be adjusted to bring the microscopy samples into focus. In order to produce an in focus image, the objective should be positioned at an appropriate distance from the focal plane for a microscopy sample. The distance between the objective and the focal plane for a microscopy sample may be referred to as the focal position of the objective.

The microscopy samples may reside at various measurement locations (e.g., wells) on the upper surface of the sample holder. The upper surface of the sample holder may thus correspond to the focal plane for a microscopy sample. Accordingly, the objective of the microscopy imaging system may be positioned at a focal position relative to the bottom of the sample holder in order to obtain an in focus image of a microscopy sample. Variations in the thickness or curvature of the sample holder, however, may prevent accurate focus over a range of measurement locations. As a result, the focal position of the objective may need to be corrected at each measurement location in order to obtain respective in focus images for all measurement locations. Because high content screenings may image hundreds or thousands of measurement samples, some microscopy imaging systems may be configured to automatically perform focus maintenance at each measurement location.

Some example microscopy imaging systems may automatically adjust the position of the objective using laser beams and a linear detector. In these example types of microscopy imaging systems, an off-axis laser beam is directed towards the lower surface of the sample holder where the beam is then reflected off the lower surface, back through the objective, and onto the linear detector. Because the laser beam directed towards the sample holder is off-axis, the position of the reflected laser beam on the linear detector thus corresponds to the position of the objective relative to the lower surface of the sample holder. If the objective moves to a new position relative to the lower surface of the sample holder, then the reflected laser beam will also move to a new position on the linear detector. The objective, in this instance, may be manually positioned at a focal position, and the corresponding position of the reflected laser beam on the linear detector may be recorded. Whenever a new measurement location is imaged, the current position of the reflected laser beam on the linear detector may be compared to the recorded position on the linear detector. If the current position of the reflected laser beam differs from the recorded position, then the position of the objective relative to the lower surface of the sample holder may be adjusted until the current position of the reflected laser beam on the linear detector matches the recorded position. The objective may also be offset from the focal position where the offset corresponds to the thickness of the sample holder. Offsetting by thickness, however, may not be accurate enough, in some circumstances, to achieve an optimal focus position unless additional focus information is provided by an image autofocus or a manual focus.

In these example types of microscopy imaging systems, however, multiple laser beams may be reflected off the lower surface, the top surface, or both the lower surface and the top surface of the sample holder. Reflected laser beams may not be distinguishable from one another. Accordingly, the reflected laser beam striking the linear detector may have originated at the upper surface or the lower surface of the sample holder. Additionally, multiple reflected laser beams may strike the linear detector in this example. As a result, adjustment of the objective may be inaccurate causing images of the microscopy samples to be out of focus. The problem of multiple reflections may be particularly pronounced where the microscopy system seeks to identify the top surface of the sample holder from below.

Other example microscopy imaging systems may also use laser beams to automatically adjust the position of the objective. In these other example types of microscopy imaging systems, the focal position for the objective is determined based on an observed peak laser beam intensity. In this example, the focal position for the objective is determined to be the position that results in the most intense (i.e., brightest or smallest) laser beam reflection. Because both the lower surface and the upper surface will reflect the laser beam, however, a search procedure may be necessary to distinguish the location of the lower surface from the upper surface of the sample holder. The objective is positioned at decreasing distances relative to the sample holder, and reflected laser beam intensities are observed at each position. Accordingly, a peak laser beam intensity may result at both the lower surface and the upper surface of the sample holder. In this example, the first peak laser beam intensity typically corresponds to the lower surface of the sample holder, and the second peak laser beam intensity typically corresponds to the upper surface of the sample holder. The position of the objective corresponding to the second peak laser beam intensity is thus identified as the focal position for the microscopy sample.

In these other example types of microscopy imaging systems, searching for both the lower surface and the upper surface of the sample holder can be time-consuming where the sample holder includes hundreds or thousands of measurement locations. These other example types of microscopy imaging systems may be configured to attempt to search only for the upper surface. Reflections from the lower surface may, however, interfere with reflections from the upper surface of the sample holder thus increasing the likelihood that the search for the upper surface will fail. If the search for the upper surface fails, these other types of example microscopy imaging systems may resort to searching for both the lower surface and the upper surface of the sample holder thus increasing the processing time of the imaging procedure.

Therefore, improved systems and methods for determining a focal position of an objective of a high content screening microscopy imaging system are needed.

SUMMARY

A method of determining a focal position for an objective positioned at a measurement location of a sample holder in a microscopy imaging system is provided. The objective is moved to a position relative to the sample holder that corresponds to a distance between the objective and the sample holder. The sample holder has a conditioned upper surface. A focusing light beam is projected onto the sample holder when the objective is located at the position, and the objective focuses the focusing light beam on the sample holder. A reflected light beam resulting from reflection of the focusing light beam off the conditioned upper surface is observed. The focal position for the objective is determined based on the reflected light beam such that the objective produces an in focus image of a microscopy sample when the objective is located at the focal position.

A microscopy imaging system is also provided. A sample holder supports a microscopy sample residing at a measurement location of the sample holder. The sample holder has a conditioned upper surface. An objective is positionable at a position relative to the sample holder that corresponds to a distance between the objective and the sample holder. A focusing light beam generator is configured to project a focusing light beam onto the sample holder, and the objective focuses the focusing light beam on the sample holder. A controller is coupled to the objective and controls the movement of the objective relative to the sample holder. The controller also determines a focal position for the objective based on a reflected light beam resulting from reflection of the focusing light beam off the conditioned upper surface such that the objective produces an in focus image of the microscopy sample when the objective is located at the focal position.

A sample holder for supporting a microscopy sample to be imaged by a microscopy imaging system is further provided. The sample holder includes a conditioned upper surface. When a focusing light beam is projected onto the sample holder, a reflected light beam results from reflection of the focusing light beam off the conditioned upper surface. The reflected light beam is stronger relative to reflected light beams that do not result from reflection of the focusing light beam of the conditioned upper surface of the sample holder.

BRIEF DESCRIPTION OF THE DRAWINGS

The invention may be better understood by referring to the following figures. The components in the figures are not necessarily to scale, emphasis instead being placed upon illustrating the principles of the invention. In the figures, like reference numerals designate corresponding parts throughout different views.

FIG. 2A is an example of an implementation of a sample holder having a conditioned upper surface.

FIG. 2B is another example of an implementation of a sample holder having a conditioned upper surface.

FIG. 7A is an illustration of light beam reflections on a sample holder that does not have a conditioned upper surface.

DETAILED DESCRIPTION

A system and method for determining the focal position of an objective of a high content screening microscopy imaging system are provided. The upper surface of the sample holder is conditioned in order to improve the detection of reflected laser beams resulting from the projection of a focusing laser beam onto the sample holder. For example, a reflective coating may be applied to the upper surface of a sample holder that improves the detection of reflected laser beams. The microscopy imaging system uses the improved reflections to determine the focal position for the objective when imaging a microscopy sample at a measurement location.

Figure 1:
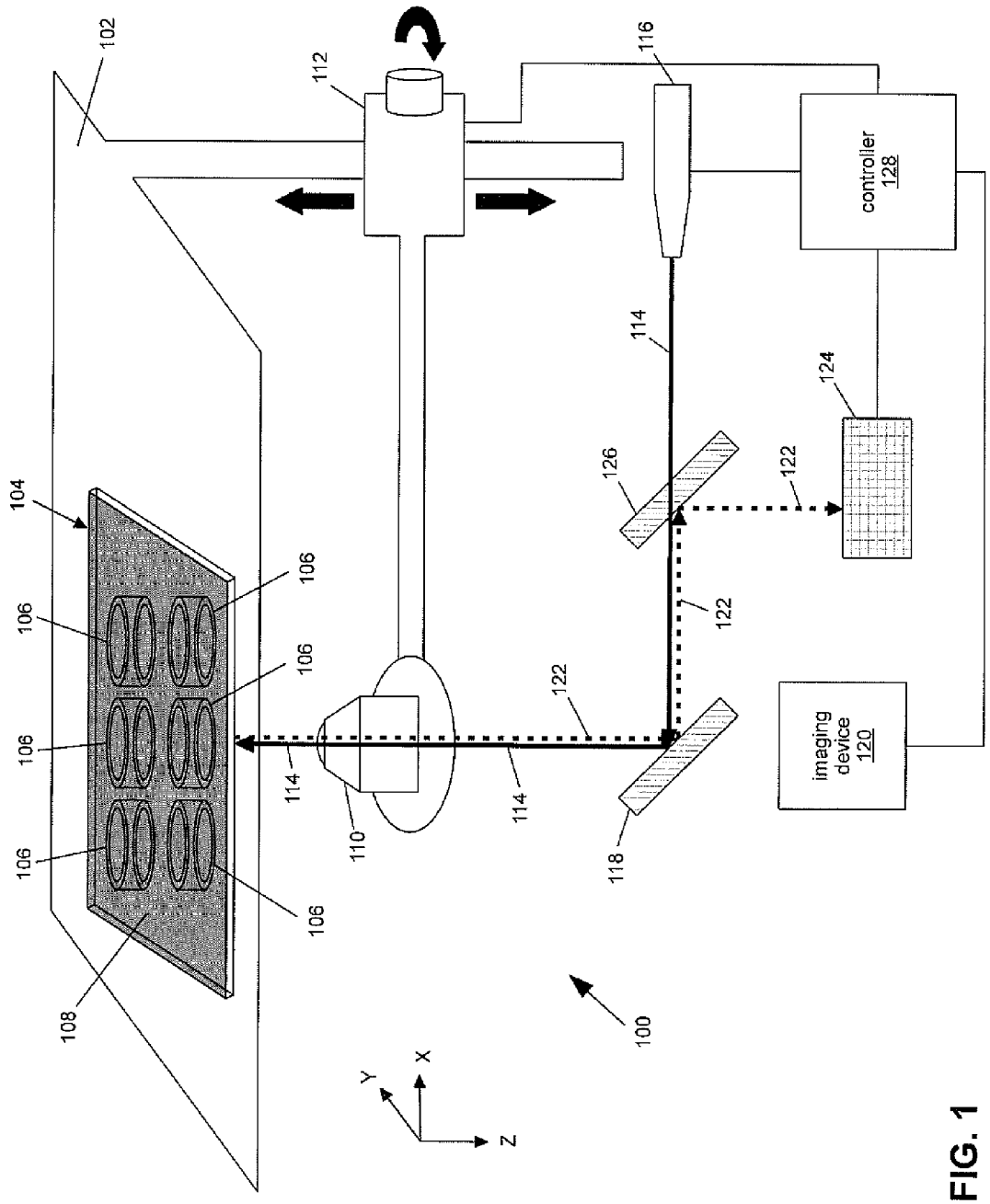
FIG. 1 is an example of an implementation of a high content screening microscopy imaging system having a sample holder with a conditioned upper surface.

Referring to FIG. 1, an example of an implementation of a high content screening (HCS) microscopy imaging system 100 is shown. A stage 102 supports a sample holder 104 containing microscopy samples to be imaged. The sample holder 104 may be, for example, a microtitre plate (i.e., microplate), a slide, a dish, or any other structure to support one or more microscopy samples to image. The sample holder 104 shown by way of example in FIG. 1 is a microplate that includes multiple wells 106 on the upper surface 108. As seen in FIG. 1, and as discussed further below, the upper surface 108 of the sample holder 104 is conditioned to improve the detection of laser beams reflected off the sample holder 104.

An objective 110 is positioned below the sample holder 104 to produce the images of the sample supported by the sample holder 104 during the microscopy imaging procedure. An aperture (not shown) formed in the bottom of the stage 102 may expose the sample holder to the objective 110 below. The objective 110, in this example, is attached to a focus motor 112 that controls the position of the objective 110 relative to the sample holder 104. As seen in FIG. 1, the sample holder 104 may be described as residing in the XY-plane. Accordingly, the focus motor 112 may position the objective 110 relative to the sample holder 104 along the Z-axis. Thus, the focus motor 112 may also be referred to as the Z-axis controller or the Z-motor, and the position of the objective 110 along the Z-axis may be referred to as the Z-position of the objective 110. As seen in FIG. 1, the focus motor 112 may position the objective 110 relatively closer to or relatively farther from the sample holder 104.

In the example microscopy imaging system 100 shown in FIG. 1, laser beams 114 are used to determine the focal position of the objective 110. Accordingly, the microscopy imaging system 100, in this example, includes a focusing light beam generator 116 (i.e., beam generator, laser beam generator, light beam generator, etc.). The focusing light beam generator 116 may generate a focusing light beam 114 such as, for example, a laser beam. The focusing light beam generator 116 may direct the focusing beam 114 towards the objective 110, which projects the focusing beam 114 onto the sample holder 104. As shown by way of example, the microscopy imaging system 100 may include a focusing beam mirror 118 to direct the focusing beam 114 from the focusing light beam generator 116 to the objective 110. The focusing beam mirror 118 may be positioned at an angle relative to the objective 110 and the focusing light beam generator 116 as shown by way of example in FIG. 1.

Focal position, in this example, refers to the distance between the objective 110 and the focal plane of the microscopy sample to be imaged. As seen in FIG. 1, the upper surface 108 of the sample holder supports the microscopy samples, thus the focal plane of the microscopy samples is located at the upper surface 108 of the sample holder 104 in this example. Positioning the objective 110 at the focal position for a particular measurement location enables the microscopy imaging system 100 to obtain an in-focus image of the microscopy sample at that measurement location. As explained further below, the microscopy imaging system 100 provided advantageously accounts for variations in the thickness and curvature of the sample holder 104 when determining respective focal positions by using the conditioned upper surface 108 of the sample holder 104.

The focal plane may also be a fixed or variable distance above the sample. The focus position may be offset before acquiring an image of the sample in order to adjust for the distance from upper surface 108 of the sample holder 104 to the sample focus position. If the distance varies more than the depth of field of an imaging device 120, the system 100 may only give an approximate focus position and further focusing via images of the sample may be performed to determine the optimal focal plane. Nonetheless, identifying the upper surface 108 is advantageous since the search range used to determine the optimal focal position is reduced.

The microscopy imaging system 100 may take various approaches to determine the focal position for the objective 110 during the microscopy imaging procedure. According to one example approach, the microscopy imaging system 100 may determine the focal position for the objective 110 based on the respective intensities of reflected light beams 122 resulting from reflection of the focusing light beam 114 off the conditioned upper surface 108 of the sample holder 104. Accordingly, the microscopy imaging system 100 may include an imaging device 120 such as, for example, a camera, to capture the respective intensities of the reflected light beams 122. In some example implementations, a mirror (not shown) may reflect the image of the sample toward an imaging device 120 such as, for example, a CMOS camera (Complementary Metal-Oxide-Semiconductor).

According to another example approach, the microscopy imaging system 100 may determine the focal position for the objective 110 based on the position at which a reflected light beam 122 strikes a linear detector 124. The position at which the reflected light beam 122 strikes the linear detector 124 thus corresponds to the position of the objective 110 relative to the sample holder 104. Like the example approach above, the reflected light beam 122 results from the reflection of the focusing light beam 114 off the conditioned upper surface 108 of the sample holder 104. As seen in FIG. 1, the microscopy imaging system 100 may also include a reflected beam mirror 126 to direct a reflected light beam 122 that is reflected off the sample holder 104 and the focusing beam mirror 118 to the linear detector 124. The reflected beam mirror 126 may be positioned at an angle relative to the linear detector 124 as shown by way of example in FIG. 1.

These example approaches for determining the focal position of the objective 110 will be discussed in further detail below with reference to FIG. 4 and FIG. 6. It will also be understood that, while the example microscopy imaging system 100 shown in FIG. 1 includes components used for both approaches described above, microscopy imaging systems may include the components used for only one of the approaches described above—either an imaging device 120 for capturing the intensities of the reflected light beams 122 or a linear detector 124 for detecting the position of reflected light beams 122 on the linear detector 124.

Still referring to FIG. 1, the microscopy imaging system 100 also includes a controller 128 for controlling the procedure for identifying the focal position of the objective 110. Accordingly, the controller 128 may be coupled to the focus motor 112, the focusing light beam generator 116, the imaging device 120, and the linear detector 124. The controller 128 may communicate with these components (e.g., issue commands or receive feedback) during the procedure for identifying the focal position of the objective 110. The controller 128 may communicate with these components using any format and protocol suitable to issue commands and receive feedback.

The controller 128 may control actuation of the focus motor 112 in order to position the objective 110. In response to receipt of commands from the controller 128, the focus motor 112 may move the objective 110 along the Z-axis to various positions relative to the sample holder 104. The controller 128 may also issue commands to the focusing light beam generator 116 in order to generate focusing light beams 114 during the procedure to identify the focal position for the objective 110. The controller 128 may issue commands to the imaging device 120 in order to obtain images of the respective intensities of reflected light beams 122, and the controller 128 may receive the images from the imaging device 120 in response. The controller 128 may also receive signals from the linear detector 124 corresponding to the respective positions that reflected light beams 122 strike the linear detector 124.

Accordingly, the controller 128 may include various control modules (not shown) for interfacing with the focus motor 112, focusing light beam generator 116, imaging device 120, and linear detector 124. The control modules may be implemented as software, hardware, or a combination of software and hardware. The controller 128 may also include other software or hardware components (not shown) used to facilitate the procedure for determining a focal position for the objective 110. For example, the controller 128 may include: a processing module having one or more processing units for processing information (e.g., reflected light beam intensities, etc.) related to the focal position determination procedure; and a memory module having one or more volatile or non-volatile memory units for storing information (e.g., images, signal values, control settings, etc.) related to the focal position determination procedure.

The controller 128 may also control movement of the optics into and out of the light path. For example, the controller 128 may move the mirrors 118 and 126 into the light path when projecting the focusing light beam 114 on the sample holder 104 and remove the mirrors 118 and 126 when acquiring images of the sample. Similarly, the controller 128 may move wavelength filters, neutral density filters, and other types of filters (not shown) into and out of the image path when imaging the sample. The controller 128 may move these components to various positions so that the focusing light beam 114 will reach the sample unimpeded.

Referring now to FIG. 2A and FIG. 2B, examples of implementations of sample holders 200 and 202 having conditioned upper surfaces 204 respectively are shown. In this example, the upper surfaces 204 have been conditioned to include a reflective coating 208 respectively. The sample holders 200 and 202 shown by way of example in FIG. 2A and FIG. 2B are microplates having multiple wells 210 positioned on the upper surface 204 of the sample holders 200 and 202.

The wells 210, in this example, are used to contain the microscopy sample for the microscopy imaging procedure.

As seen in FIG. 2A and FIG. 2B, the reflective coatings 208 may be applied to at least a portion of the upper surface 204 of the microplates 200 and 202. In FIG. 2A, the reflective coating 208 is applied to the entirety of the upper surface 204 of the microplate 200. In FIG. 2B, the reflective coating 208 is only applied to the portion of the upper surface 204 bounded by the wells 210 of the microplate 202. Additional or alternative covering patterns may be selectively employed. Moreover, the reflective coating 208 may be configured such that the reflective coating 208 is reflective of the specific wavelength of the focusing light beam 114 (FIG. 1).

Various approaches may be employed to apply the reflective coating 208 to the upper surface 204 of the sample holders 200 and 202. For example, one approach may dispense a solution across the upper surface 204 of a sample holder that chemically interacts with the upper surface 204. The reflective coating 208 may remain on the upper surface 204 of the sample holder when the solution is subsequently rinsed off of the upper surface 204. Where the sample holder includes wells 210 like the sample holders 200 and 202 in this example, the solution may be dispensed on the upper surface 204 before the wells 210 are attached to the upper surface 204 of the sample holders 200 and 202.

The composition of the reflective coating 208 may be an organic compound provided in solution. In this case, a solution-based coating technique may be used to form a film on the upper surface 204, such as spin-coating, spray-coating, flow-coating, or dip-coating. If the coating is only to be applied in the wells 210 (like FIG. 2B), then the solution may be sprayed through a patterned mask. The mask may be initially attached to the upper surface 204, the reflective coating 208 may then be applied through the windows of the mask, and the mask may be removed. Solution-based coating may be followed by a drying step to remove excess solvent from the reflective coating 208 via evaporation. The drying step may be assisted by heat or vacuum. After the reflective coating 208 is applied, the reflective coating 208 may be cured so as to harden it, which may involve heating or exposure to UV light (ultraviolet), X-ray, or other type of energy.

The composition of the reflective coating 208 may be a metal or an inorganic compound. In the case of a metal compound, the coating technique may be a metallization technique such as utilized those in the microelectronics industry, e.g., electroplating or thermal evaporation. In the case of either a metal or an inorganic compound, the coating technique may be a vacuum deposition technique such as those utilized in the microelectronics or microfabrication industries, e.g, physical vapor deposition, sputter deposition, or chemical vapor deposition. If the reflective coating 208 is only to be applied in the wells 210 (like FIG. 2B), then deposition may be followed by a suitable patterning or etching technique, i.e., photolithography.

Apart from applying a solution or implementing a deposition technique, the reflective coating 208 may initially be provided in the form of a preexisting sheet, foil, or dry film. In this case, the reflective coating may be applied to the sample holders 200 and 202 as a lamination in which case an adhesive may be used. Commercially available adhesives exist that are specified as being highly optically transparent and therefore may not interfere with the laser beam. Alternatively to an adhesive, the preexisting sheet may be a material that only needs to be heated where the application of heat may be sufficient for the material to self-adhere to the underlying upper surface 204 of the sample holders 200 and 202.

The reflective coating 208 applied to the upper surface 204 of the sample holders 200 and 202 may, in some implementations, be combined with a biologically active or a chemically active coating. As an example, a coating that fluoresces in the presence of a particular protein may be employed. Additionally, a coating that has properties to help the cells adhere to the upper surface 204 of the sample holders 200 and 202 may be employed.

Additionally, a polarized coating may be employed as an alternative to a reflective coating. Where a polarized coating is used, the polarized coating may block light of a particular polarization (i.e., light waves extending in a specific orientation in the X-Y axis) from reflecting off the sample holders 200 and 202 since laser light is polarized by its nature. Additionally, a filter may be employed to polarize non-polarized light. In addition to reflective coatings and polarized coatings, the upper surface 204 of the sample holders 200 and 202 may alternatively be conditioned to include a fluorescent coating. Other techniques to condition the upper surface 204 of the sample holders 200 and 202 may also be selectively employed. For example, conditioning the upper surface 204 of the sample holders 200 and 202 may include etching the upper surface 204 with micro-etched lines. The spacing between the micro-etched lines may correspond to the wavelength of the light thereby providing polarization or color reflectance. Another alternative to provide the conditioned the upper surface 204 of the sample holders 200 and 202 may be to include colored media in the wells 210 of the sample holders 200 and 202.

Reflections off the conditioned upper surface 204 of the sample holders 200 and 202 will thus be stronger (e.g., more intense, brighter, etc.) relative to reflections off the bottom surface 212 of the sample holders 200 and 202 (or the transparent surfaces of a conventional sample holder) that is not conditioned. As a result, a microscopy imaging system 100 (FIG. 1) that uses a sample holder (e.g., sample holder 200 or 202) having a conditioned upper surface 204 may more quickly and more accurately locate the upper surface 204 corresponding to the focal plane for the microscopy samples supported on the upper surface 204. In this way, determining the focal position for the objective 110 (FIG. 1) is advantageously less complex, less time-consuming, and less prone to error.

Figure 3:
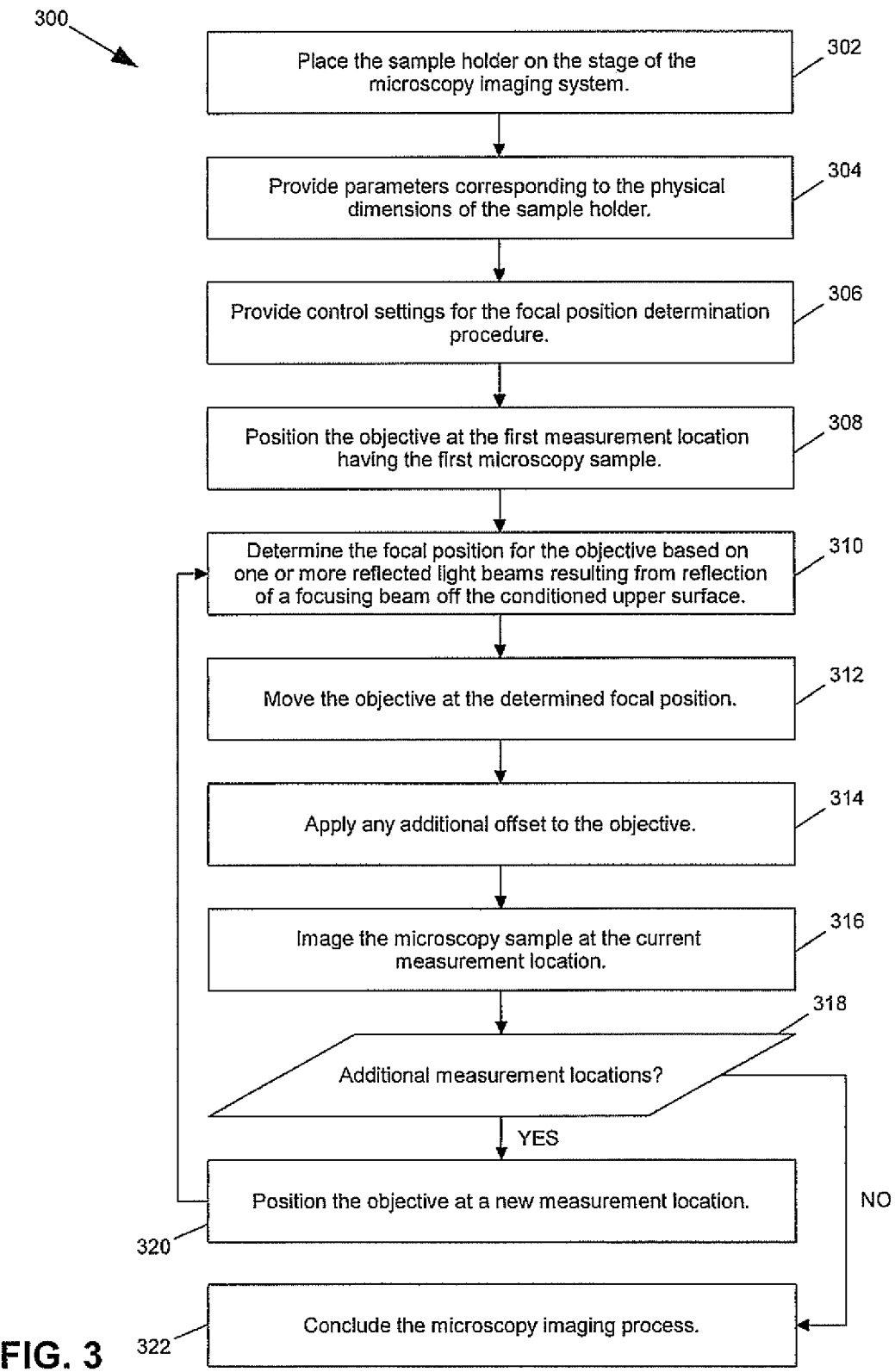
FIG. 3 is a flowchart of example method steps for imaging microscopy samples using a sample holder having a conditioned upper surface.

Referring now to FIG. 3, a flowchart 300 of example method steps for imaging microscopy samples using a sample holder having conditioned upper surface of the sample holder is shown. A user places the sample holder on the stage of the microscopy imaging system (step 302). The user may provide the microscopy imaging system with parameters corresponding to the physical dimensions of the sample holder (step 304). For example, the user may provide parameters corresponding to the length, width, and thickness of the sample holder as well as the number or measurement locations at the sample holder. The user may also provide control settings for the focal position determination process (step 306). For example, the user may provide for the intensity of the focusing light beam, Z-axis step size, Z-axis range. The control settings may also correspond to the operation of the imaging device such as, for example, an exposure time. The parameters for the sample holder and the configuration settings may be manually provided by the user or, additionally or alternatively, stored by the microscopy imaging system itself as hard-coded values.

The Z-motor may move in discrete units. Accordingly, the Z-motor may move 10 microns at a time during a search. The Z-axis range refers to the distance the Z-motor should move during the search. For example, when moving between wells, the Z-axis range is the distance the Z-motor should move when searching for the new focal position at the new well. The Z-axis range should be sufficient to accommodate the difference in height along the Z-axis between one well and the next without being too large such that the objective comes into contact with the sample holder during the search.

The microscopy imaging system may then image the microscopy samples residing at the various measurement locations of the sample holder. To begin the imaging process, the objective may be positioned at the first measurement location having the first microscopy sample to image (step 308). The objective may be positioned at the measurement locations by, for example, moving the objective itself, moving the sample holder that includes the measurement locations, or moving the stage that supports the sample holder.

As discussed above, variations in the thickness or curvature of the sample holder may cause individual microscopy samples to be located in different focal planes. As a result, the microscopy imaging system may determine the focal position for the objective used to image the microscopy samples at each measurement location. The microscopy imaging system determines the focal position for the objective based on one or more reflected light beams resulting from the reflection of a focusing light beam off of the conditioned upper surface of the sample holder (step 310). Example approaches to determining the focal position for the objective will be discussed in further detail below with reference to FIG. 4 and FIG. 6. Once the focal position for the objective is determined, the objective is moved to the determined focal position (step 312). If desired, an additional offset may be applied to the objective (step 314).

An additional offset may be applied where chromatic aberrations are expected. Due to the properties of the lenses in the system, the focal distance to the same object may vary slightly based on the wavelength of light. In some cases, the thickness of the sample may shift the focal point away from the upper surface. With adherent cells, for example, the nucleus of the cell is often thicker than the cytoplasm. It may be desirable then to shift to a focus position in the middle of the nucleus to obtain the most in-focus data possible for imaging the nucleus. A typical nucleus size is often known, so the shift may be fixed for the entire collection of samples. Similarly, it may be desirable to apply an additional offset in order to shift to the middle of a tissue sample. Additionally, other materials included on the upper surface of the sample holder by the manufacturer or the user may require applying additional offsets to obtain an optimal focus position since the samples may rest on these additional materials.

In this way, the objective produces an in-focus image of the microscopy sample at the current measurement location. The microscopy imaging system thus images the microscopy sample at the current measurement location of the sample holder (step 316). If the sample holder includes additional measurement locations (step 318), then the objective may be positioned at a new measurement location (step 320) and the microscopy imaging system may repeat steps 310-316 in order to image the respective microscopy samples at the additional measurement locations. As seen in FIG. 3, the microscopy imaging system may determine the focal position for the objective for each microscopy sample at each measurement location in order to account for any variations in the thickness or curvature of the sample holder across a range of measurement locations. If the sample holder does not include any additional measurement locations (step 320), then the microscopy imaging system may conclude the microscopy imaging process (step 322).

Figure 4:
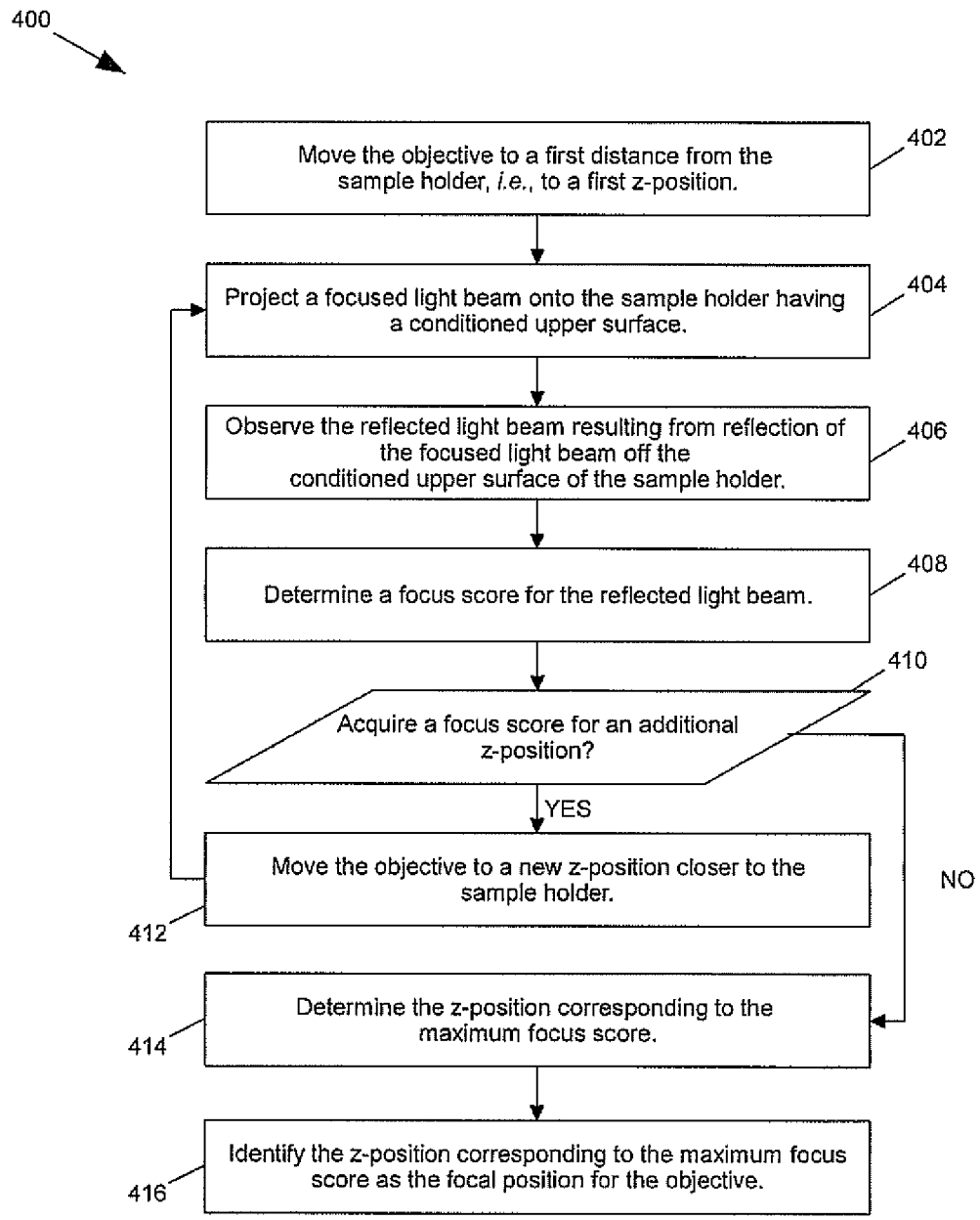
FIG. 4 is a flowchart of example method steps for determining the focal position for an objective based on light beams reflected off the conditioned upper surface of a sample holder.

Referring now to FIG. 4, a flowchart 400 of example method steps for determining the focal position for an objective based on light beams reflected off the conditioned upper surface of a sample holder is shown. As shown by way of example in FIG. 1 above, the objective may be positioned below the stage that supports the sample holder. Accordingly, the objective, in this example, may be moved to a first a first distance (i.e., z-position) below the sample holder (step 402).

A focusing light beam is projected onto the sample holder, which includes a conditioned upper surface, e.g., a reflective coating applied to the upper surface of the sample holder (step 404). The focusing light beam is thus reflected off of the conditioned upper surface of the sample holder as a reflected light beam. The reflected light beam resulting from the reflection of the focusing light beam off the conditioned upper surface of the sample holder is then observed (step 406) in order to determine a focus score for the reflected light beam (step 408).

As an example, the microscopy imaging system may include an imaging device such as, for example, a camera that obtains (captures) an image of the reflected light beam. The microscopy imaging system may analyze the image of the reflected light beam in order to determine a focus score for the reflected light beam. The focus score may be based on, for example, the brightness of the reflected light beam as observed in the captured image or, additionally or alternatively, the size of the reflected light beam observed in the captured image. The size of the reflected light beam may be determined, for example, by measuring the diameter of the reflected light beam in the captured image. A relatively brighter reflected light beam and a relatively smaller reflected light beam may respectively correspond to a relatively higher focus score.

The microscopy imaging system, in this example, thus determines the focal position for the objective based on the respective focus scores corresponding to the z-positions of the objective. Accordingly, the microscopy imaging system may determine that the focal position for the objective is the z-position that corresponds to the brightest reflected light beam or, additionally or alternatively, the smallest reflected light beam.

The microscopy imaging system may determine focus scores for multiple z-positions of the objective. If there are additional z-positions (step 410), then the microscopy imaging system may move the objective to a new z-position closer to the sample holder (step 412) and repeat steps 404-408 in order to obtain a focus score for the new z-position. The microscopy imaging system may use the Z-axis step size to determine how far the objective should be moved when moving the objective to a new z-position. As the objective is moved closer to the sample holder, the brightness of the reflected light beam should increase until the brightness reaches a peak (i.e., maximum brightness) at which point the brightness of the reflected light beam begins to decrease. Likewise, the size of the reflected light beam should decrease as the objective is moved closer to the sample holder until the size of the reflected light beam reaches a peak (i.e., smallest size) at which point the size of the reflected light beam begins to increase. The z-position resulting in the observed peak (maximum focus score) is thus the position for the objective along the Z-axis that results in an in focus image of the microscopy sample, i.e., the focal position for the objective.

If there are no additional z-positions to determine focus scores for (step 410), then the microscopy imaging system determines the z-position corresponding to the maximum focus score (step 414). The microscopy imaging system, in this example, thus identifies the z-position corresponding to the maximum focus score as the focal position for the objective (step 416). Due to the conditioned upper surface of the sample holder, light beams reflected off the upper surface of the sample holder are relatively stronger than any light beams reflected off the lower surface of the sample holder. In this way, the microscopy imaging system can more reliably and quickly locate the upper surface of the sample holder and by extension more accurately determine the focal position for the objective.

Figure 5A:
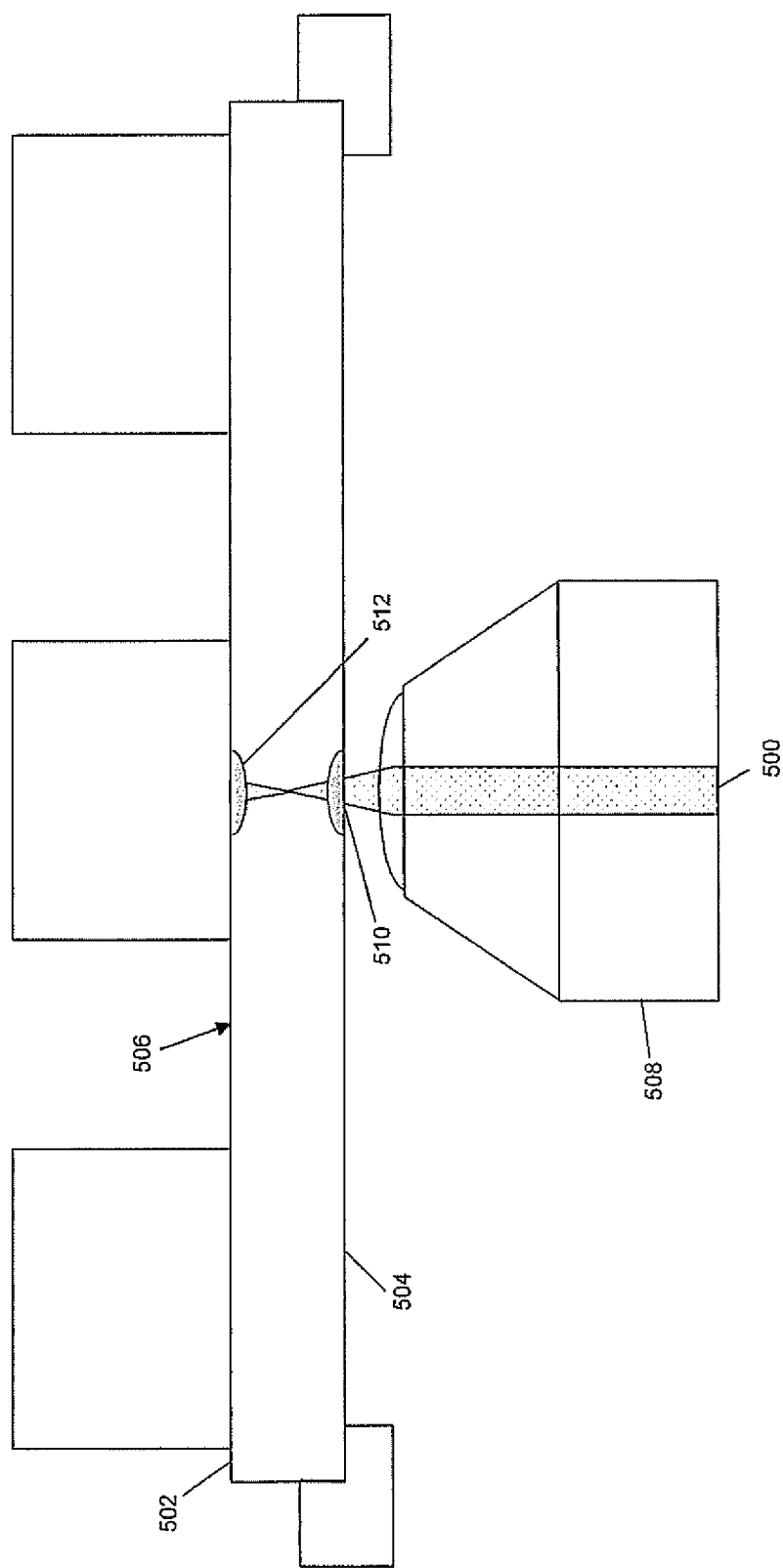
FIG. 5A is an illustration of light beams reflected off a sample holder that does not have a conditioned upper surface.

FIG. 5A illustrates reflections of a focusing light beam 500 off an upper surface 502 and a lower surface 504 of a sample holder 506 where the upper surface 502 is not conditioned. In the example shown in FIG. 5A, the objective 508 focuses a focusing light beam 500 on the sample holder 506 from below. The focusing light beam 500 results in two reflected light beams 510 and 512 off of the sample holder 506: a light beam reflection 510 reflected off the lower surface 504 of the sample holder 506 and a light beam reflection 512 reflected off the upper surface 502 of the sample holder 506. The reflected light beams 510 and 512 are depicted in FIG. 5A as two gray half-ovals on the lower surface 504 and the upper surface 502 of the sample holder 506 respectively. As seen in FIG. 5A, the two reflected light beams 510 and 512 may be approximately equal in intensity or size when the objective 508 is not in focus. As a result, the reflected beams 510 and 512 off the lower surface 504 and the upper surface 502 respectively may cause confusion when attempting to locate the upper surface 502.

Figure 5B:
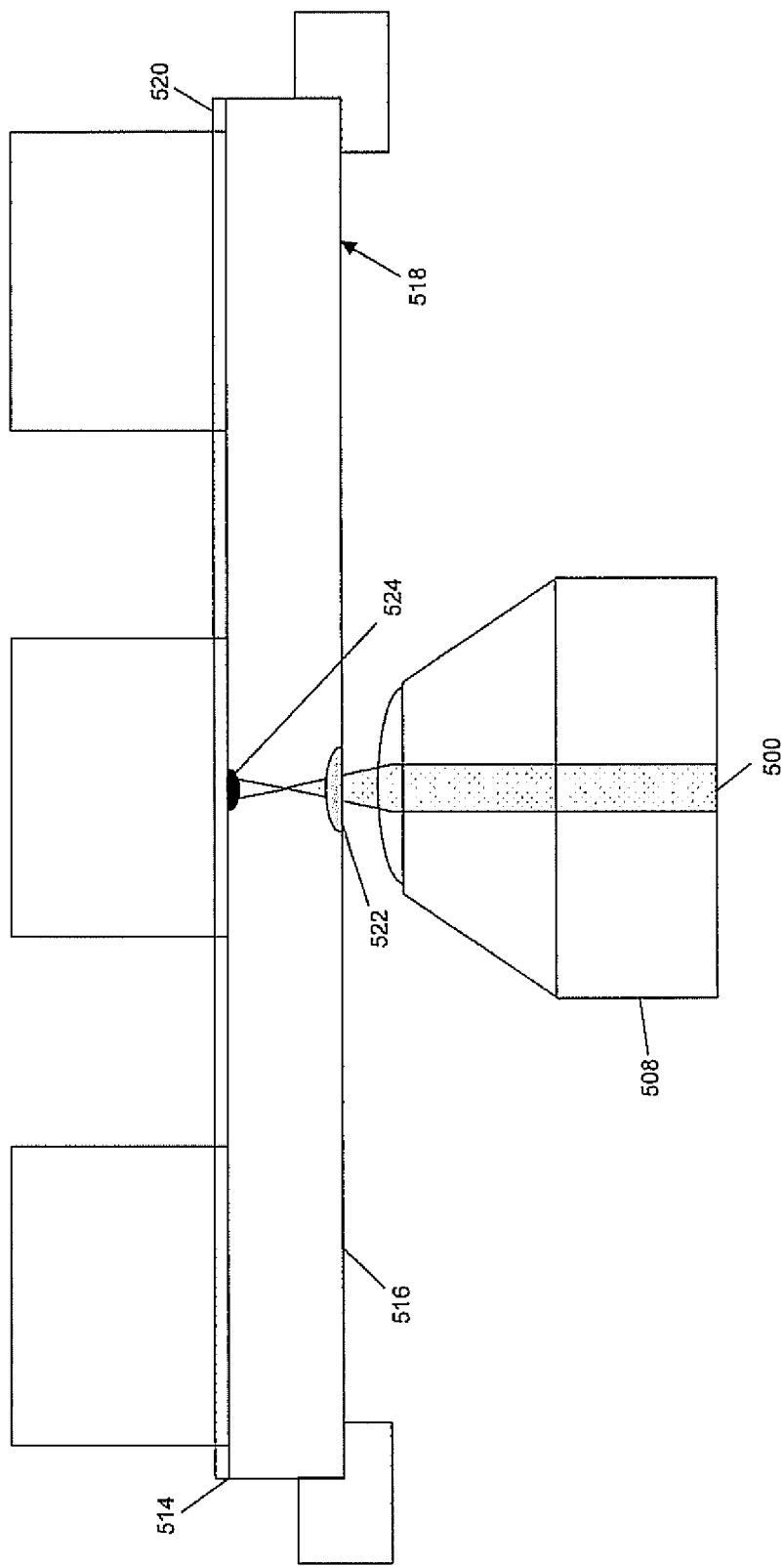
FIG. 5B is an illustration of light beams reflected off an example of an implementation of a sample holder having a conditioned upper surface.

In contrast, FIG. 5B illustrates reflections of a focusing light beam 500 off an upper surface 514 and a lower surface 516 of a sample holder 518 that does include a conditioned upper surface. In this example, the upper surface 514 of the sample holder 518 is conditioned to include a light-reflective property (or an enhanced light-reflective property), such as by including a reflective coating 520. In the example shown in FIG. 5B, the objective 508 likewise focuses the focusing light beam 500 on the sample holder 518 from below. The focusing light beam 500 in FIG. 5B also respectively results in reflected light beams 522 and 524 off the lower surface 516 and the upper surface 514 of the sample holder 518 respectively. The reflected light beams 522 and 524 are also depicted in FIG. 5B as half-ovals on the lower surface 516 and the upper surface 514 of the sample holder 518 respectively. In contrast to FIG. 5A, however, the light beam 524 reflected off the reflective coating 520 applied to the upper surface 514 is relatively stronger (as depicted by a relatively smaller and darker half-oval) than the light beam 522 reflected off the lower surface 516 (as depicted by a relatively larger and lighter-colored half-oval).

In this way, the microscopy imaging system 100 (FIG. 1) may advantageously identify the upper surface 514 of the sample holder 518 based on the relatively stronger reflected light beam 524 that results from reflection of the focusing light beam 500 off the conditioned upper surface 514 of the sample holder 518. Accordingly, the microscopy imaging system 100 may ignore the relatively weaker reflected light beam 522 off the lower surface 516 of the sample holder 518. For example, the imaging device 120 (FIG. 1) that captures an image of the brightness or the size of the reflected light beam 524 may be configured with a relatively lower exposure time such that the relatively weaker reflected light beams 522 off the lower surface 516 of the sample holder 518 are below the background noise in the captured image and thus not captured by the imaging device 120. In this example, the imaging device 120 would capture the relatively stronger light beams 524 reflected off the conditioned upper surface 514 and ignore the relatively weaker light beams 522 reflected off the lower surface 516 of the sample holder 518 that is not conditioned.

As another example, the microscopy imaging system 100 (FIG. 1) may be configured with a reflection threshold such that the imaging device 120 (FIG. 1) only captures reflected light beams above the reflection threshold (e.g., the reflected light beam 524 of the conditioned upper surface 514 of the sample holder 518) when determining the focus score for the z-position. The reflection threshold may be set such that light beams 522 reflected off the lower surface 516 of the sample holder 518 fall below the reflection threshold and light beams 524 reflected off the upper surface 514 of the sample holder 518 fall above the reflection threshold. In this way, the imaging device 120 would similarly capture the relatively stronger light beams 524 reflected off the conditioned upper surface 514 and ignore the relatively weaker light beams 522 reflected off the lower surface 516 of the sample holder 518.

Figure 6:
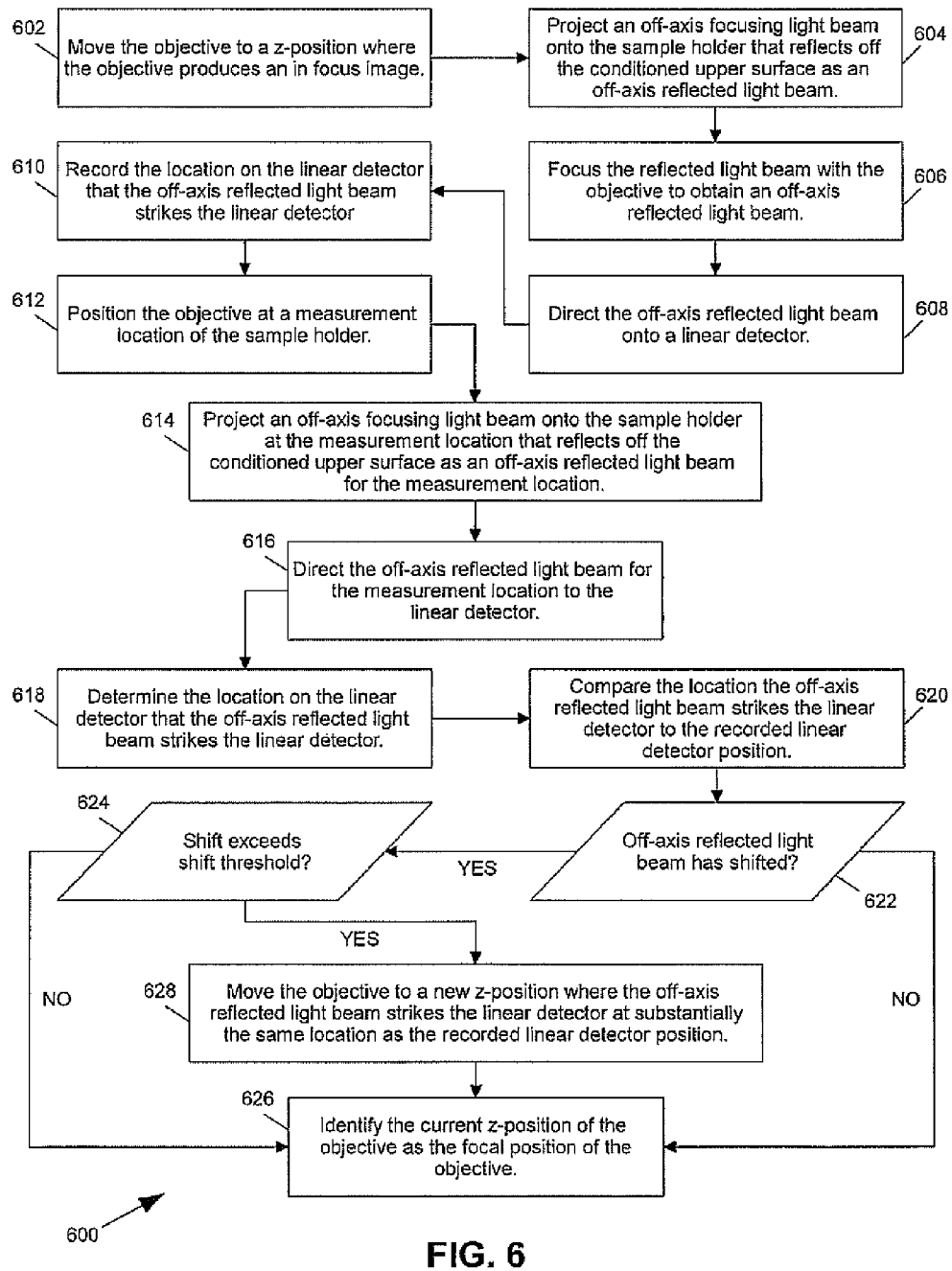
FIG. 6 is another flowchart of example method steps for determining the focal position of an objective based on light beams reflected off the conditioned upper surface of a sample holder.

Referring now to FIG. 6, another flowchart 600 of example method steps for determining the focal position of an objective based on light beams reflected off the conditioned upper surface of a sample holder is shown. First, the objective is moved to a z-position where the objective produces an in focus image, i.e., a focused z-position (step 602). In this example, a user may manually move the objective to a z-position that produces the in focus image of the microscopy sample and determine that the image is in focus by sight (e.g., by driving the Z-motor with a joystick).

The microscopy imaging system may then project an off-axis focusing light beam onto the sample holder (step 604). In this example, the objective may be described as oriented around a central axis. Accordingly, an off-axis focusing light beam in this example refers to a focusing light beam parallel with the central axis of the objective but located radially away from the central axis of the objective. The off-axis focusing beam, in this example, reflects off the conditioned upper surface of the sample holder as a reflected light beam and reenters the objective. Accordingly, the objective focuses the reflected light beam to obtain an off-axis reflected light beam (step 606). Like an off-axis focusing light beam, an off-axis reflected light beam, in this example, refers to a reflected light beam parallel with the central axis of the objective but located radially away from the central axis of the objective. An off-axis focusing light beam and an off-axis reflected light beam are shown by way of example in FIG. 7A and FIG. 7B.

The microscopy imaging system, in this example, then directs the off-axis reflected light beam onto a linear detector (step 608). As discussed above with reference to FIG. 1, the microscopy imaging system may include one or more mirrors to direct the off-axis reflected light beam onto the linear detector. The microscopy imaging system then records the location that the off-axis reflected light beam strikes on the linear detector (step 610). The recorded location on the linear detector (i.e., focused linear detector location) thus corresponds to a z-position that produces an in focus image when the objective is positioned at that z-position.

Having recorded the location on the linear detector that corresponds to a z-position resulting in an in focus image, the microscopy imaging system may then position the objective at a measurement location having a microscopy sample to image (step 612). As mentioned above, the microscopy imaging system may position the objective at a measurement location by, for example, moving the objective itself, moving the sample holder that includes the measurement locations, or moving the stage that supports the sample holder.

With the objective positioned at a measurement location having a microscopy image to sample, the microscopy imaging system projects an off-axis focusing light beam onto the sample holder at the current measurement location (step 614). The focusing light beam reflects off the reflective coating applied to the upper surface of the sample holder as a reflected light beam, and the objective focuses the reflected light beam to obtain an off-axis reflected light beam. The microscopy imaging system directs the off-axis reflected light beam for the current measurement location onto the linear detector.

The microscopy imaging system determines the location that the off-axis reflected light beam for the current measurement location strikes the linear detector (step 616). The microscopy imaging system then compares the current linear detector location for the off-axis reflected light beam to the recorded linear detector location (step 618). The microscopy imaging system compares the current linear detector location to the recorded linear detector location to determine whether the location on the linear detector has shifted (step 620). As explained above, the location on the linear detector may shift where the distance between the objective and the sample holder changes due to the use of an off-axis focusing light beam and corresponding off-axis reflected light beam. Accordingly, variations in the thickness and curvature of the sample holder may result in varying distances between the sample holder and the objective. As a result, these variations in the thickness and curvature of the sample holder may cause the location on the linear detector to shift.

If the microscopy imaging system determines that the current location on the linear detector has shifted (step 622)—i.e., the current linear detector location does not match the recorded linear detector location)—then the microscopy imaging system may determine whether the shift is significant enough to move the objective to a new z-position in order to refocus the objective (step 624). The microscopy imaging system may determine whether the shift is significant enough by comparing the size of the shift to a shift threshold. The Z-motor may have an effective minimum move size or maximum accuracy. For example, if the maximum accuracy of the Z-motor is 500 nm (nanometers) then a shift of 200 nm should be ignored. Similarly, the depth of field of the imaging system may be known, which may be determined by the samples. If the depth of field of the objective is 2 μm (micrometers), then it may not be desirable to adjust for a shift of 0.5 μm since no improvement of focus would be expected. If the size of the shift does not exceed the shift threshold, then the microscopy imaging system may determine that the objective is still in focus and identify the current z-position of the objective as the focal position for the objective (step 626).

If, however, the microscopy imaging system determines that the shift does exceed the shift threshold (step 624), then the microscopy imaging system may move the objective to a new z-position where the off-axis reflected light beam strikes the linear detector at a location that does not exceed the shift threshold (step 628). The microscopy imaging system may determine the new z-position based on the difference between the current linear detector location and the recorded linear detector location. In other words, the distance between the current linear detector location and the recorded linear detector location may correspond to a movement distance along the Z-axis. The microscopy imaging system may move the objective to the new z-position by moving the objective along the Z-axis over the movement distance (corresponding the difference between the current linear detection location and the recorded linear detection location). The microscopy imaging system may then identify this new z-position as the focal position for the objective (step 626). The microscopy imaging system may repeat steps 602-626 at each measurement location in order to determine the focal position for the objective at each measurement location.

In some example implementations, there may be no minimum shift. For example, a non-computerized system may output a current from the linear detector, and the Z-motor may be continually adjusted based on the current from the linear detector with no practical lower limit and no reason to interfere with the feedback by introducing a threshold. It will also be understood that a camera may be employed in this fashion to monitor shifting of the reflected light beam based on the location of the reflected light beam in an image.

FIG. 7A illustrates an off-axis focusing beam 700 used to focus an objective 702 for a sample holder 704 where the upper surface 706 is not conditioned. As seen in FIG. 7A, an off-axis focusing beam 700 is projected onto the sample holder 704 from below. The off-axis focusing beam 700, in this example, is parallel with the central axis 708 of the objective 702 but located radially away from the central axis 708. The objective 702 directs the off-axis focusing beam 700 on the sample holder 704, and the sample holder 704 reflects the focusing light beam 700 as reflected light beams 710, 712, and 714.

In the example shown in FIG. 7A, the off-axis focusing light beam 700 reflects off both the lower surface 716 and the upper surface 706 of the sample holder 704. The focusing light beam 700 is shown by way of example in FIG. 7A as a solid line. Reflected light beams 710 and 712 are shown by way of example in FIG. 7A as dashed lines. In this example, the lower surface 716 of the sample holder 704 reflects the off-axis focusing light beam 700 as the focusing light beam 700 enters the sample holder 704 thereby resulting in reflected light beam 710. The off-axis focusing light beam 700 travels through the sample holder 704 to the upper surface 706 and reflects off the upper surface 706 back through sample holder as reflected light beam 712. The lower surface 716 of the sample holder deflects the reflected light beam 712 as the reflected light beam 712 exits the sample holder resulting in deflected light beam 714. The deflected light beam 714 is also shown in this example as a dashed line.

The reflected and deflected light beams 710, 712, and 714 shown by way of example in FIG. 7A may have a comparable intensity or strength. As a result, the linear detector 124 (FIG. 1) may not be able to distinguish light beams 710 reflected off the lower surface 716 of the sample holder 704 (or deflected light beams 714) from light beams 712 reflected off of the upper surface 706 of the sample holder 704. Therefore, the linear detector 124 of the microscopy imaging system 100 (FIG. 1) may not be able to accurately determine whether the objective 702 should be refocused.

Figure 7B:
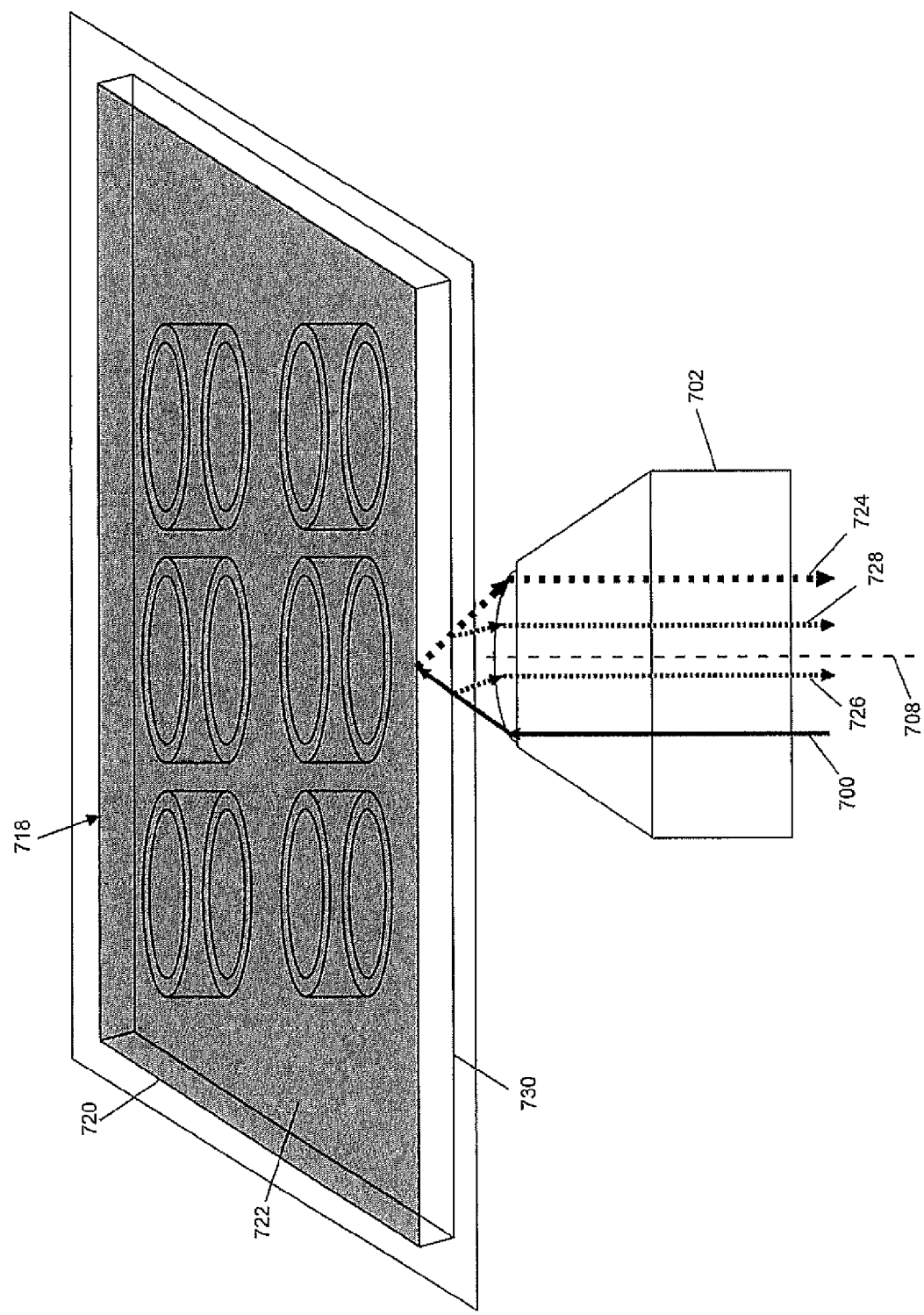
FIG. 7B is an illustration of light beam reflections on an example of an implementation of a sample holder having a conditioned upper surface.

In contrast, FIG. 7B illustrates an off-axis focusing beam 700 used to focus an objective 702 for a sample holder 718 that does include a conditioned upper surface 720. In this example, the upper surface 720 of the sample holder 718 has been conditioned to include a reflective coating 722. As seen in FIG. 7B, the off-axis focusing light beam 700 reflects off the reflective coating 722 applied to the upper surface 720 of the sample holder 718. The reflection of the focusing light beam 700 off the reflective coating 722 thus results in a reflected light beam 724 that is relatively stronger than the reflected light beam 726 and the deflected light beam 728 off the lower surface 730 of the sample holder 718. The relatively stronger reflected light beam 724 is depicted in FIG. 7B as a relatively thicker dashed line.

Accordingly, the light beams 726 and 728 respectively reflected and deflected by the lower surface 730 shown by way of example in FIG. 7B are relatively weaker than the light beam 724 reflected by the reflective coating 722 applied to the upper surface 720 of the sample holder 718. As a result, in contrast to FIG. 7A, the linear detector 124 may advantageously distinguish light beams 726 and 728 reflected and deflected by the lower surface 730 of the sample holder 718 from light beams 724 reflected off the reflective coating 722 of the upper surface 720. The linear detector 124 may be configured to thus monitor the strongest reflected light beam it receives, which, in this example, results from the reflection of the focusing light beam 700 off the reflective coating 722 applied to the upper surface 720 of the sample holder 718.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A method of determining a focal position for an objective positioned at a measurement location of a sample holder in a microscopy imaging system, the method comprising:
    positioning the objective at a z-position along a Z-axis relative to the sample holder;
    moving the objective to a plurality of z-positions relative to the sample holder, the sample holder having a conditioned upper surface of the sample holder and the plurality of z-positions corresponding to a respective distance between the objective and the sample holder;
    projecting a focusing light beam onto the sample holder when the objective is located at individual z-positions in the plurality of z-positions, the objective focuses the focusing light beam on the sample holder;
    observing a reflected light beam resulting from reflection of the focusing light beam off the conditioned upper surface of the sample holder;
    observing a plurality of reflected light beams resulting from reflection of the focusing light beam off the reflective coating, where plurality of reflected light beams respectively correspond to the individual z-positions and respectively corresponding to a plurality of focus scores;
    determining which focus score in the plurality of focus scores is a maximum focus score; and
    identifying the z-position in the plurality of z-positions that corresponds to the maximum focus score as the focal position for the objective.

2. The method of claim 1 where the conditioned upper surface includes a reflective coating applied to the upper surface and.

3. The method of claim 2 where at least one of the reflected light beams in the plurality of reflected light beams is a relatively strong reflected light beam in relation to relatively weak reflected light beams that do not result from reflection of the focusing beam off the reflective coating applied to the upper surface of the sample holder and further comprising:
    receiving a control setting corresponding to operation of an imaging device configured to image the relatively strong reflected light beam;
    obtaining an image of the relatively strong reflected light beam with the imaging device using the control setting;
    determining the focus score corresponding to the relatively strong reflected light beam based on the image of the relatively strong reflected light beam; and
    where the control setting is selected such that the image does not include the relatively weak reflected light beams.

4. The method of claim 3 where the control setting is an exposure time, the exposure time is selected such that the imaging device images the relatively strong reflected light beam during the exposure time and does not image the relatively weak reflected light beams during the exposure time.

5. The method of claim 3 where the control setting is a reflection threshold, the reflection threshold is selected such that the relatively strong reflected light beam is above the reflection threshold and imaged by the imaging device and such that the relatively weak reflected light beams are below the reflection threshold and are not imaged by the imaging device.

6. The method of claim 3 further comprising determining the focus score corresponding to the relatively strong reflected light beam based on a brightness or a size of the relatively strong reflected light beam observed in the image of the relatively strong reflected light beam.

7. The method of claim 3 further comprising:
    moving the objective to the z-position that corresponds to the maximum focus score; and
    imaging the microscopy sample while the objective is located at the z-position that corresponds to the maximum focus score.

8. The method of claim 1 where the conditioned upper surface includes a reflective coating applied to the upper surface further comprising:
    directing the reflected light beam onto a linear detector such that the reflected light beam strikes a location on the linear detector;
    comparing the location on the linear detector to a recorded linear detector location, the recorded linear detector location corresponds to a focused z-position that results in an in focus image when the objective is located at the focused z-position;
    determining whether the location on the linear detector has shifted away from the recorded linear detector location; and
    in response to a determination that the location on the linear detector has shifted away from the recorded linear detector location, determining a new z-position for the objective based on the comparison of the location on the linear detector to the recorded linear detector location and identifying the new z-position as the focal position for the objective.

9. The method of claim 8 further comprising configuring the linear detector to monitor a strongest reflected light beam in a plurality of reflected light beams directed onto the linear detector where the strongest reflected light beam results from reflection of the focusing light beam off the reflective coating applied to the upper surface of the sample holder.

10. A microscopy imaging system comprising:
    a sample holder that supports a microscopy sample residing at a measurement location of the sample holder, the sample holder having a conditioned upper surface of the sample holder;
    an objective positionable at a z-position along a Z-axis relative to the sample holder;
    a focusing light beam generator configured to project a focusing light beam onto the sample holder when the objective is located at individual positions in the plurality of z-positions;
    a plurality of reflected light beams respectively corresponding to the individual z-positions, the plurality of reflected light beams resulted from reflection of the focusing light beam off the conditioned upper surface of the sample holder;
    a controller coupled to the objective, the controller moving the objective to the plurality of z-positions relative to the sample holder, where the plurality of z-positions correspond to respective distances between the objective and the sample holder; and where the controller
determines a focal position for the objective based on a reflected light beam such that the objective produces an in focus image of the microscopy sample when the objective is located at the focal position, determines a plurality of focus scores respectively corresponding to the plurality of reflected light beams, determines a maximum focus score in the plurality of focus scores, and identifies the z-position in the plurality of z-positions that corresponds to the maximum focus score as the focal position for the objective.

11. The system of claim 10 where at least one of the reflected light beams in the plurality of reflected light beams is a relatively strong reflected light beam in relation to relatively weak reflected light beams that do not result from reflection of the focusing light beam off the reflective coating applied to the upper surface of the sample holder and further comprising:
   an imaging device that obtains an image of the relatively strong reflected light beam using a control setting corresponding to operation of the imaging device;
   where the controller determines the focus score corresponding to the relatively strong reflected light beam based on the image of the relatively strong reflected light beam; and
   where the control setting is selected such that the image does not include the relatively weak reflected light beams.

12. The system of claim 11 where the control setting is an exposure time, the exposure time is selected such that the imaging device images the relatively strong reflected light beam during the exposure time and does not image the relatively weak reflected light beams during the exposure time.

13. The system of claim 11 where the control setting is a reflection threshold, the reflection threshold is selected such that the relatively strong reflected light beam is above the reflection threshold and imaged by the imaging device and such that the relatively weak reflected light beams are below the reflection threshold and are not imaged by the imaging device.

14. The system of claim 11 where the controller determines the focus score corresponding to the relatively strong reflected light beam based on a brightness or a size of the relatively strong reflected light beam observed in the image of the relatively strong reflected light beam.

15. The system of claim 11 where:
   the controller moves the objective to the z-position that corresponds to the maximum focus score; and
   the imaging device images the microscopy sample residing at the measurement location while the objective is located at the z-position that corresponds to the maximum focus score.

16. The system of claim 10 where the conditioned upper surface includes a reflective coating applied to the upper surface and further comprising:
   a linear detector coupled to the controller, the linear detector receives the reflected light beam such that the reflected light beam strikes a location on the linear detector;
   where the controller compares the location on the linear detector to a recorded linear detector location, the recorded linear detector location corresponds to a focused z-position that results in an in focus image when the objective is located at the focused z-position;
   where the controller determines whether the location on the linear detector has shifted away from the recorded linear detector location; and
   where, in response to a determination that the location on the linear detector has shifted away from the recorded linear detector location, the controller determines a new z-position for the objective based on the comparison of the location on the linear detector to the recorded linear detector location and identifies the new z-position as the focal position for the objective.

17. The system of claim 16 where the linear detector is configured to monitor a strongest reflected light beam in a plurality of reflected light beams directed onto the linear detector where the strongest reflected light beam results from reflection of the focusing light beam off the reflective coating applied to the upper surface of the sample holder.

18. The microscopy imaging system of claim 10, where the conditioned upper surface of the sample holder includes at least one of:
   (a) a reflective coating applied to at least a portion of the upper surface of the sample holder;
   (b) a polarized coating applied to at least a portion of the upper surface of the sample holder;
   (c) a fluorescent coating applied to at least a portion of the upper surface of the sample holder;
   (d) lines etched into at least a portion of the upper surface of the sample holder; and
   (e) a colored medium applied to at least a portion of the upper surface of the sample holder.

* * * * *